(12) United States Patent
Kvitash

(10) Patent No.: US 6,768,948 B2
(45) Date of Patent: Jul. 27, 2004

(54) BALASCOPY SYSTEM AND METHOD WITH IMPROVED SENSITIVITY

(76) Inventor: Vadim Kvitash, 2299 Post St. #306, San Francisco, CA (US) 94115

( * ) Notice: Subject to any disclaimer, the term of this patent is extended or adjusted under 35 U.S.C. 154(b) by 74 days.

(21) Appl. No.: 10/282,512

(22) Filed: Oct. 29, 2002

(65) Prior Publication Data

US 2004/0083059 A1 Apr. 29, 2004

(51) Int. Cl.$^7$ .............................................. G06F 19/00
(52) U.S. Cl. ......................................... 702/19; 600/300
(58) Field of Search ............................. 702/19–22, 67, 702/179–181, 187, 189; 128/920–925; 600/300, 301, 509; 345/440, 805; 426/634

(56) References Cited

U.S. PATENT DOCUMENTS

| | | | |
|---|---|---|---|
| 4,527,240 A | * | 7/1985 | Kvitash ........................ 702/19 |
| 5,731,998 A | * | 3/1998 | Lotito et al. .................. 702/189 |
| 6,246,903 B1 | * | 6/2001 | Kletskin ....................... 600/509 |
| 6,292,761 B1 | * | 9/2001 | Hancock, Jr. ................ 702/189 |

OTHER PUBLICATIONS

J.H. Siegel "Relationships between circulatory and specific changes in Sepsis", 32, Ann. Rev. Med. (Annual Reviews, Inc, 1981) 175–194.

"Patient Data Systems" General Electric Med. Systems Critical Care Medicine , Jan./Feb. 1976.

J.Parenteral and Enternal Nutrition, 499,1980 S, Nazarl et al.

* cited by examiner

Primary Examiner—Marc S. Hoff
Assistant Examiner—Mohamed Charioui

(57) ABSTRACT

The method and system improve the balascopic concept disclosed in U.S. Pat. No. 4,527,240 by introducing relative balascopic units more convenient for graphical representation of parameters in a multiple-parametric system. The "analysis-of-pair" method is improved by replacing the graphical linear representation with balascopic vectors, which show a direction of changes of the relationship from normal and the length of which corresponds to the amount of the change. The circular diagram method is improved by dimensisonlessly rescaling the balascopic units into a system in which deviations for all parameters are shown from mean statistic values recalculated on the same radius of the circular diagram. According to another embodiment for balascopic representation of diagnostic data, the circular diagram of the invention are developed into a linear form.

45 Claims, 11 Drawing Sheets

FIG. 4
PRIOR ART

| BU | 64 | 35 | 26 | 66 | 14 | 6 | 13 | 4 | 9 | 39 | 37 | 57 | |
|---|---|---|---|---|---|---|---|---|---|---|---|---|---|
| ACT. VAL. (Mg/dl OR V/l) | 4.2 | 8.8 | 3.6 | 330 | 183 | 84 | 665 | .6 | 15 | 8.4 | 218 | 7.1 | ← PARAMETER |
| | 1 | 2 | 3 | 4 | 5 | 6 | 7 | 8 | 9 | 10 | 11 | 12 | |
| 1 | | N | N | CI 96% | CN 6% | N | CN 9% | N | N | CN 22% | N | N | |
| 2 | | | N | NI | CN 22% | CN 3% | CN 27% | N | N | CI 20% | NI | N | |
| 3 | | | | FI 12% | N | N | CN | N | N | NI | N | N | |
| 4 | | | | | FI 49% | FN | FN 51% | FN 59% | FI 53% | NI | NI | CI 80% | |
| 5 | | | | | | FN 3% | N | FN | NI | N | N | N | |
| 6 | | | | | | | FN 5% | N | N | FN 4% | N | N | |
| 7 | | | | | | | | FN 4% | NI | N | N | CN 4% | |
| 8 | | | | | | | | | N | FN 4% | N | N | |
| 9 | | | | | | | | | | FN 4% | N | N | |
| 10 | | | | | | | | | | | NI | CN 22% | |
| 11 | | | | | | | | | | | | N | |

IMBALANCE ↗ (arrow pointing to row 3/4 area)

LEGEND:
N = NORMAL
CN = CLOSER THAN NORMAL
FN = FARTHER THAN NORMAL
NI = NORMAL & INVERTED
CI = CLOSER & INVERTED
FI = FARTHER & INVERTED

FIG. 5A
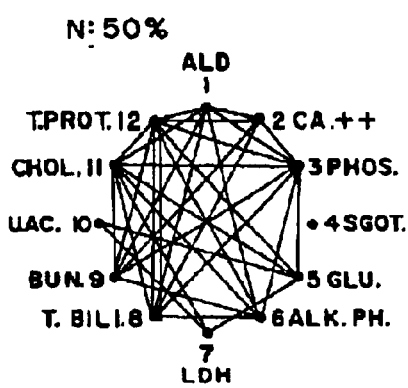
FIG. 5B
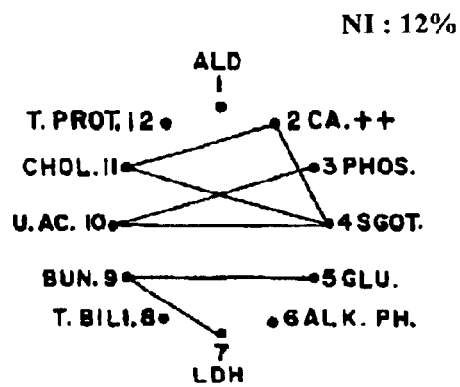
FIG. 5C
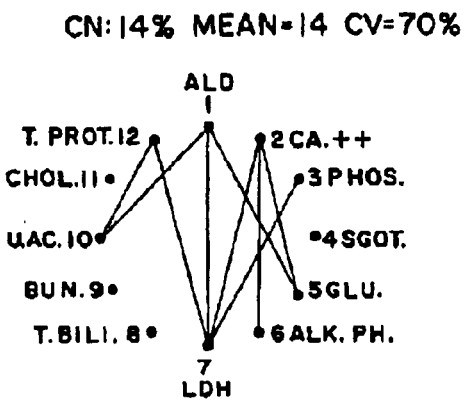
FIG. 5D
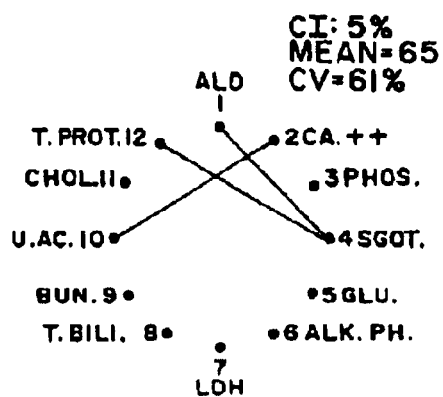
FIG. 5E
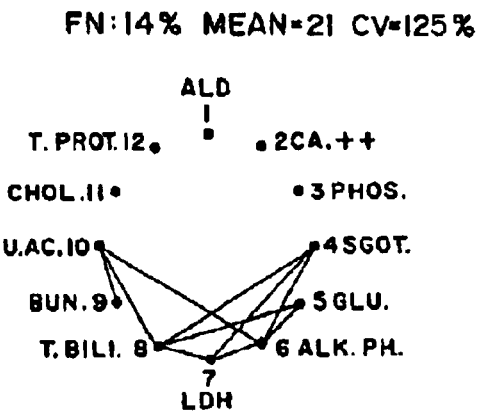
FIG. 5F
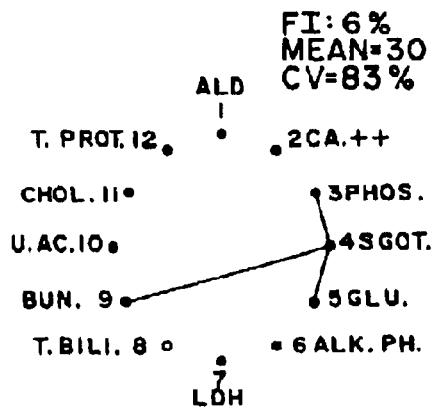
FIG. 5 PRIOR ART

|    | 1          | 2         | 3         | 4         | 5         | 6         | 7         | 8       | 9       | 10        | 11        | 12        |
|----|------------|-----------|-----------|-----------|-----------|-----------|-----------|---------|---------|-----------|-----------|-----------|
| 1  | 64<br>4.2% | N         | N         |           | CN<br>6%  | N         | CN<br>9%  | N       | N       | CN<br>22% | N         | N         |
| 2  |            | 35<br>8.8 | N         |           | CN<br>22% | CN<br>3%  | CN<br>27% | N       | N       |           |           | N         |
| 3  |            |           | 26<br>3.6 |           | N         | N         | CN        | N       | N       |           | N         | N         |
| 4  | CI<br>96%  | NI        | FI<br>12% | 66<br>3.30|           | FN<br>51% | FN<br>59% | FN      |         |           |           |           |
| 5  |            |           |           | FI        | 14<br>13.3| FN<br>3%  | N         | FN      |         | N         | N         | N         |
| 6  |            |           |           |           |           | 6<br>84   | FN<br>5%  | N       | N       | FN<br>4%  | N         | N         |
| 7  |            |           |           |           |           |           | 13<br>665 | FN<br>4%|         | N         | N         | CN<br>4%  |
| 8  |            |           |           |           |           |           |           | 4<br>6  | N       | FN<br>4%  | N         | N         |
| 9  |            |           |           | FI<br>53% | NI        |           | NI        |         | 9<br>15 | FN<br>4%  | N         | N         |
| 10 |            | CI<br>20% | NI        | NI        |           |           |           |         |         | 39<br>8.4 |           | CN<br>22% |
| 11 |            | NI        |           | NI        |           |           |           |         |         | NI        | 37<br>218 | N         |
| 12 |            |           |           | CI<br>80% |           |           |           |         |         |           |           | 57<br>7.1 |

FIG. 10

BALASCOPY SYSTEM AND METHOD WITH IMPROVED SENSITIVITY

FIELD OF INVENTION

The present invention relates to the detection and evaluation of multiple imbalances within multi-parametric systems, particularly to the employment of graphic means for performing such detections and evaluations. It is particularly useful in the field of medicine for the diagnosis and follow-up treatment of diseases. It may be used in many other fields for evaluating, diagnosing, predicting, analyzing, describing behavior, change of behavior, etc., where multiple parameters in a related system are involved.

BACKGROUND OF THE INVENTION

In medicine, for optimal care and therapy, quantitative as well as qualitative judgments of the degrees of abnormalities should be made when diagnosing patients. Previous studies have suggested that an analysis of combinations of laboratory data of a patient may be of greater aid in understanding the patient's condition than an analysis of individual items of data per se.

Heretofore one scientific method of diagnosing diseases from laboratory data has used a statistical analysis of deviations of a patient's data from a normal range. The results obtained were arranged in the form of a circular coordinate system which employed radial axes calibrated according to the patient's laboratory parameters, with standard deviations of each parameter plotted on the respective axes. Following this, a pattern was created by interconnecting adjacent points on the axes. Diagnosis was performed by comparing the obtained pattern of an individual patient with reference patterns typical for certain diseases. J. H. Siegel, "Relations Between Circulatory and Specific Changes in Sepsis," 32 Ann. Rev. Med. (Annual Reviews, Inc. 1981) 175–194; also see the "Patient Data System," General Electric Medical Systems (adv't.), Critical Care Medicine, January/February 1976.

While useful, these methods did not provide sufficient information for one to detect pathology with normal data and did not reveal qualitative and quantitative types of imbalances between parameters.

Another method has been suggested in an attempt to overcome these difficulties. This method was similar to the previous ones: a circular type representation of parameters on radial axes was provided with values plotted on the radial axes, but expressed as a percentage of normal values, rather than by standard deviations. S. Nazari et al., "A Multivariable Pattern for Nutritional Assessment," 4 J. Parenteral and Enteral Nutrition 499, 1980.

This method provided more distinguishable patterns than the previous one because the percentage scale was more sensitive than the standard deviation scale. Nevertheless this method still did not provide sufficient information for one to obtain quantities and qualitative types of imbalances between parameters and did not reveal any multiple imbalances which were present within the system.

In order to overcome disadvantages of the aforementioned known methods and systems, the applicant have developed a new diagnostic system based on so-called balascopic units which is described in U.S. Pat. No. 4,527,240 issued to the applicant in 1985 and incorporated herein by reference. In this system, relationships between multiple related parameters, such as blood chemistry data, are evaluated by converting the data into specially normalized units as a percentage on a scale depicting the maximum and minimum empirical values for such parameter.

The essence of the balascopy consists of transformation of measured values into dimensionless balascopic scales. The balascopic units used in these scales are dimensionless and are based on the following assumptions.

Let us assume that $P_{max}$ is the maximum value ever measured for a certain parameter, e.g., serum protein and that that $P_{min}$ is the minimum value ever measured for serum protein. These values are obtained from the existing data based on large amounts of available measurements. Let us designate the difference between $P_{max}$ and $P_{min}$ as $\xi$, i.e., $$P_{max} - P_{min} = \xi = \text{Const (mg/dl)}$$

Let us introduce an inverse scale based on 100 units based on the following transformation:

$$100/\xi = \eta = \text{Const (dl/mg)}.$$

The measured value of the parameter is designated as $P_{mes}$ (mg/dl). The same parameter obtained from the available statistical data for healthy people is designated as $P_{mes\,(st.norm)}$.

Let us subtract $P_{min}$ from $P_{mes}$ and designate the result of subtraction as v, i.e., $$P_{mes} - P_{min} = v\,(\text{mg/dl})$$

It is understood that for a live person u is always greater than 0. A balascopic unit $P_{bu}$, on which the previous and the present invention of applicant are based, is equal to:

$$P_{bu} = (100/\xi) \cdot v\,(\text{dimensionless})$$

$P_{bu}$ is always less than 100.

It is obvious that the value of $P_{bu}$ corresponding to $v_{norm} = P_{mes(st.\,norm)} - P_{min}$, i.e., $P_{bu\,norm} = (100/\xi) \cdot v_{norm}$ is an average statistical value of a selected parameter for a healthy person, e.g., of serum protein, expressed in balascopic units.

A main advantage of transfer to balascopic units is the use of large statistic data obtained for healthy and unhealthy people ($P_{max}$ and $P_{min}$).

For example, the empirically existing maximum of the total serum protein in vivo comprises 11.0 milligrams (mg) of protein per tenth liter (deciliter—dl) of blood, and the minimum is 2.0 mg/dl. The range between these values is thus 11.0−2.0=9.0 mg/dl. This range is then converted into special normalized units on a scale of 100, such that each normalized unit will correspond to 100/9=11.1 actual units (in mg/dl). A patient's measured total serum protein value may be thus converted to normalized units by subtracting the minimum actual value from the patient's actual value and then multiplying the result by 11.1 or by 100/9.

For example, if a patient's measured total serum protein is 7.3 mg/dl, this value is made the minuend, the minimum empirical value (2.0 mg/dl), is made the subtrahend, and the difference, 5.3 mg/dl, is determined. This difference (5.3 mg/dl) is then multiplied by the normalized unit value, 11.1, to provide a special normalized value according to the invention, which is 58.9 units.

The applicant have designated these special normalized units (regardless of the parameter represented) by the term Balascopic units, where "bala" stems from the word "balanced" and "scopic" stems from the Greek word "observe". Thus it is clear that the balascopic method is based on visual representation of deviation from balance.

Then a normal relationship between pairs of such data (FIG. 1—N) is provided and compared with measured relationships between corresponding pairs of data (FIG. 1—CN to FN) and quantitative and qualitative evaluations are made. Also the complete set of data for such a system is plotted on respective radial axes in such normalized units on a circular coordinate system with the respective maximum and minimum for each parameter being marked on its radius. This is shown in FIG. 2 which is a circular diagram of a balascopic pattern for blood chemistry. This diagram contains a closed-loop contour 22 plotted for maximum values of the parameters and a closed loop contour 21 for minimum values of the parameters, while a normal closed-loop pattern, which is completely within the area defined between the contours 20 and 21 and which is $P_{bu\ st.norm}$, is an average statistical value for normal parameters of a healthy person (FIG. 2). Then measured parameters for various entities are similarly plotted and compared with the normal annulus or known abnormal annuli (FIG. 3 is a diagram of the type shown in FIG. 2 for *Diabetes mellitius* with Kimmel Stiel-Wilson disease and Secondary Hyperparathyroidism. It is understood that similar diagrams can be plotted for other diseases such as myxedema, thyrotoxicosis, etc. with deviation patterns typical of each specific disease.

Generally, laboratory data or measured parameters of a patient are used to make and confirm a diagnosis and to monitor the course of treatment. In a basic aspect of the present invention, each measured parameter of a patient is noted and is made far more useful and meaningful by expressing it as a percentage between the minimum and maximum empirical values of said parameter.

Given below are some explanations and definitions given in U.S. Pat. No. 4,527,240 and repeated here as they will be used in the present patent application.

In FIG. 1, the vertical scale is calibrated in Balascopic units (BU) from 0 to 100, with 0 BU corresponding to the existing empirical minimum and 100 BU corresponding to the existing empirical maximum of both total serum protein and serum albumin of a patient. The first (leftmost) block of this diagram (labeled Normal and N) shows how Balascopic units can be used to represent a normal relationship between these two blood parameters. In this block, point $P_N$ represents a normal value of total serum protein in a patient. The absolute value of Example 1 when converted from mg/dl—not indicated—to Balascopic units, gives 58.9 or 59 BU, as explained.

Assume further that the normal patient's serum albumin is measured in an absolute measurement (not indicated) and when converted to Balascopic units (according to the above-described method), is 70 BU. This parameter is indicated at point $A_N$.

A broken line is drawn to connect points $P_N$ and $A_N$; this line indicates the normal relationship between these two parameters. A normal differential (sometimes called "gradient") between total serum protein ($P_N$) and serum albumin ($A_N$) is thus equal to 70 BU-59 BU=11 BU. Preferably block N is made of transparent material so that it can be superimposed over any other block in FIG. 1.

In FIG. 1, the second block from the left, CN, illustrates a deviation from the normal relationship between total serum protein and serum albumin. In this case the values are Closer than Normal (CN); this closer-than-normal relationship is sometimes called an "integrated" relationship. According to the previous procedure, the two values are measured, converted to BU, and the resultant points are connected. The resultant differential between them is assumed equal to 5 BU, i.e., less than the normal differential (Block N) of 11 BU.

Since the two values P and A in blocks N and CN are plotted the same distance apart, the gradients of their interconnection lines can be easily compared by a superimposition of the normal gradient upon the actual measured gradient in block CN. The abnormality of the patient in block CN can easily be seen by the reduced slope of the solid gradient line $P_{CN}$—$A_{CN}$ in this block when compared with the normal gradient (broken line $P_N$—$A_N$).

Similarly, a type of imbalance where the two parameters are too far apart in shown in the next block, FN (Further than Normal). Here the Balascopic differential is equal to 40 BU, which is farther than the normal 11 BU differential. This "FN" (sometimes called "disintegrated") relationship can easily be seen by the increased slope of the interconnection line $P_{FN}$—$A_{FN}$, especially when compared with the superimposed normal gradient (broken line $P_N$—$A_N$) superimposed thereover.

In the next block (NI), line $P_{NI}$—$A_{NI}$, has a normal Balascopic gradient of 11 BU, but the mutual positions of the two points are inverted from normal. This type of relationship is called Normal Inverted (NI) and also is vividly demarcated by the superimposed broken line $P_N$—$A_N$.

In the next block CI (Closer and Inverted) (sometimes called "integrated" and inverted), line $P_{CI}$—$A_{CI}$ represents a close-than-normal and inverted relationship with a Balascopic gradient of 10 BU. Compare this line with the normal broken line $P_N$—$A_N$. In the last block, FI, a Farther-than-Normal and at the same time inverted relationship is shown by the line $P_{FI}$—$A_{FI}$. This Frther-than-Normal and inverted (sometimes called "disintegrated" and inverted) relationship is also vividly demarcated by the superimposed normal broken line $P_N$—$A_N$.

As will be recognized by those skilled in the art, the above method reveals five new definitive and qualitative types of imbalances between blood chemistry parameters that can be established. This method can also be used for any given pair of parameters in a system of related parametric quantities. Each of the above imbalances can be quantitatively estimated by the degree of imbalance in percent.

The relationships between many parameters in a system or related parameters can be represented simultaneously by the method illustrated by the diagram of FIG. 2. This drawing shows a circular coordinate system having twelve radial lines corresponding to twelve standard blood chemistry parameters, 1. albumin, 2. $Ca^{++}$ (Calcium ions), 3. phosphorus, 4. AST(SGOT) (serum glutamic oxytransaminase), 5. glucose, 6. alkaline phosphatase (ALK.PHOS.), 7. LDH (lactic dehydrogenose), 8. bilirubin total, 9. BUN (blood urea nitrogen), 10. uric acid, 11. cholesterol, and 12. total protein. The reference or normal range values for these parameters are plotted in normalized or Balascopic units (BU) on the respective axes in the manner aforedescribed. The mean values of these parameters are then interconnected to form a closed or endless line 20.

The shaded ring-shaped or annular area 22 in FIG. 2 shows the normal range for a healthy population chosen by conventional statistical methods. Area 22 is drawn by plotting the normal lowest and highest values for each parameter on its radial axis, and then interconnecting the lowest points and the highest points to form two closed lines (similar to line 22) and shading the area between these lines. Note that the parameters connected by line 20 all fall within the normal range. In order to simplify the visual comparison and present it in a more obvious way, the radial axes on the circular diagrams of FIG. 2 are arranged in the specific order indicated (rather than the standard sequence of a laboratory test routine) so that the boundaries limiting the normal range will define the substantially annular pattern shown. If the axes were arranged in an order corresponding to the sequence of a standard laboratory test routine, the pattern of the normal range would have been too complicated for comparison and too difficult to employ as an effective and in diagnosis.

FIG. 3 is a similar circular diagram depicting abnormal patterns of blood chemistry typical for a patient with *diabetes mellitus* with Kimmelstiel-Wilson disease and secondary hyperparathyroidism plotted as line 30.

It is understood that similar abnormal conditions can be presented in the same system for other diseases. It can be seen that the use of a circular diagram with the normal range for the blood chemistry parameters plotted as a shaded ring and the patient's parameters plotted thereover or hereunder by a solid line greatly facilitates, strengthens, and improves diagnosis, especially when prototype patterns for typical diseases (such as shown in FIG. 3) are superimposed on the diagram, either with (not shown), or in lieu of the normal annular shaded area of FIG. 2.

It is now possible and desirable to obtain a full set of the existing relationships between all parameters of blood chemistry expressed in terms of Balascopic differences or gradients. This can be seen in FIG. 4, where the blood chemistry data from a recently measured patient with a myocardial infarction (MI) and their corresponding values in Balascopic units (BU) are presented and taken from Table 1 below.

TABLE 1

BLOOD CHEMISTRY FROM PATIENT WITH MI

| Parameter No. | Parameter | Actual Value | Units | BU |
|---|---|---|---|---|
| 1 | Albumin | 4.2 | mg/dl | 64 |
| 2 | CA++ | 8.8 | mg/dl | 35 |
| 3 | Phosphorou | 3.6 | mg/dl | 26 |
| 4 | AST(SGOT) | 330 | U/l | 66 |
| 5 | Glucose | 183 | mg/dl | 14 |
| 6 | ALK.PHOS. | 84 | U/l | 6 |
| 7 | LDH | 665 | U/l | 13 |
| 8 | T. Bilirubin | 0.6 | mg/dl | 4 |
| 9 | BUN | 15 | mg/dl | 9 |
| 10 | Uric Acid | 84 | mg/dl | 39 |
| 11 | Cholesterol | 218 | mg/dl | 37 |
| 12 | Total Protein | 7.1 | mg/dl | 57 |

By way of example, consider the first line of Table 1 which shows how this patient's albumin, measured as 4.2 mg/dl, is converted to Balascopic units (BU). The lowest value of albumin measured in a living patient is 1.0 mg/dl. The highest value is 6.0 mg/dl. According to the principle of Balascopy, the difference between these maximum and minimum is taken to be 100 BU. To convert the patient's actual value of 4.2 mg/dl into BU, subtract the existing minimum (1.0) from the actual value (4.2) multiply the result by 100 divide by the difference between the existing maximum and the existing minimum (5.0) to obtain the value indicated in the rightmost column, 64 BU.

The other blood parameters for this patient have also been processed in this manner to obtain the data in the "BU" column.

Note that Table 1 above presents relatively little readily-understandable information and is difficult to analyze or evaluate, either initially, or on a follow-up monitoring, while the chart of FIG. 3 presents a readily-identifiable portrayal of the patient's pathology.

While FIG. 3 vividly depicts the patient's quantitative relationships, the chart of FIG. 4 shows the entire spectrum of all existing parametric relationships in quantitative as well as qualitative terms, and also indicates the actual and Balascopic units for each parameter. For example in the parameter row (third row down, just above double line) parameter 1 has an actual value (second row down) of 4.2 mg/dl and a value in BU (top row) of 64 units. The parameters are also indicated by number in the rightmost column, to the right of the double line.

The qualitative relationship of parameter 1 (rightmost column) with parameter 10 (third row down) is indicated to be closer than normal by the legend "CN" in the block at the intersection of parameters 1 and 10 and this relationship quantitatively is a 22 percent imbalance (same block).

These qualitative and quantitative relationships can be determined as follows: The Balascopic difference between parameter 1 (64 BU) and parameter 10 (39 BU) is 64−39=25 BU. The average Balascopic difference between these two parameters for the healthy population is 48.2 BU, with a standard deviation (SD) of 8.1 BU. Thus the Balascopic difference for a normal relationship (about 95% of the population) should lie between the limits of the average value ("X") ±2 SD. Since X is 48.2 BU, this range extends for 48.2±(2×8.1) BU or 32.0 to 64 BU.

This means that any value of Balascopic difference for a patient's parameters 1 and 10 between 32.0 and 64.4 BU can be considered a normal relationship.

In the present example, the Balascopic difference is only 25 BU, which is less than 32.0 BU and therefore is an imbalance type of relationship, a CN (Closer than Normal) type because the difference (25 BU) is less than the normal difference.

To evaluate the quantitative degree of closeness, consider the range between the lower limit of the normal difference (32 BU) and the maximum closeness (0 BU) as 100% and determine the degree of actual closeness in percent.

In the present case the lower limit of normal difference (32 BU) less the actual difference (25 BU) is divided by the lower limit (32) times 100=22 percent, as indicated in FIG. 7 in the block at the intersection of parameters 1 and 10.

The formulae above used are valid for all of the abnormal qualitative relationships indicated in FIG. 1 (CN, FN, CI, and FI).

The following Table 2 is a statistical analysis of the data in Table 1 and FIG. 4. This table shows, for the 66 existing pairs of relationships of the 12 blood parameters used, the actual number of occurrences of each type of relationship, the percentage of the total for each type of relationship, the statistical mean, in BU, of each type of relationship, and the statistical coefficient of variation for each relationship.

TABLE 2

Statistical Analysis of Relationships of FIG. 4 and Table 1

| Type of Relationship | Occurrences | Percent of Total Occurrences | Mean in BU | Coefficient of Variation |
|---|---|---|---|---|
| N | 33 | 50 | — | — |
| Nl | 8 | 12 | — | — |
| CN | 9 | 14 | 13.55 | 70 |
| FN | 10 | 15 | 21.00 | 125 |
| CI | 3 | 5 | 65.33 | 61 |
| Fl | 3 | 4 | 29.75 | 83 |

As will be appreciated by those skilled in the art, it is difficult to draw a conclusion from data presented in the above tabulation, but by processing the data and presenting it in the form of the analytical graphs with superimposed normal or known condition range values, a far clearer picture of pathology is readily presented.

FIG. 5 presents another method of graphically portraying the relationships and more vividly indicating the degree of abnormality. FIG. 5 is divided into six parts, FIGS. 5A to 5F, respectively showing the six types of specific relationships (N, CN, FN, NI, CI, and FI), as discussed for the patient with the myocardial infarct whose data are not shown but also can be presented similar to the form of FIG. 3.

Each part of FIG. 5 has 12 dots, numbered 1 to 12, spaced evenly in a circular configuration, each dot representing one of the 12 blood chemistry parameters aforediscussed. In each part of FIG. 5, every pair of parameters which have the specific relationship specified by the heading of the part is indicated by a line interconnecting the pair of dots representing the parameters which have such a specific relationship. Thus in FIG. 5A, the dots for every pair relationship which have a normal relationship, i.e., the relative values of the parameters are in the normal relationship range, are interconnected by a line. In the patient under consideration, the relative values for the following parameters are in the normal range and hence the following pairs of dots are joined in FIG. 5A: 1–2, 1–3, 1–6, 1–8, 1–9, 1–11, 1–12, 2–3, 2–8, 2–9, 2–12, 3–5, 3–6, 3–8, 3–9, 3–11, 3–12, 5–7, 5–10, 5–11, 5–12, 6–8, 6–9, 6–11, 6–12, 7–10, 7–11, 8–9, 8–11, 8–12, 9–11, 9–12, and 11–12.

Since 50% of all existing pairs of parameters are joined in FIG. 5A, this is indicated by the legend "N: 50%" meaning that 50% of the parametric relationships for this patient are normal. Obviously the more lines that are present in a "normal" diagram (FIG. 5A), the better the patient's blood chemistry condition.

In FIG. 5B, on the other hand, lines are shown for only the parametric relationships which are abnormal in the normal but inverted (NI) manner. Since this a pathalogical condition, obviously the more lines, which are present in FIG. 5B (as well as FIGS. 5C to 5F), the worse the patient's condition. As indicated in FIG. 5B, 12% of the patient's blood chemistry parametric relationships are normal-inverted (NI).

The remaining four sections, C, D, E, and F, of FIG. 5 represent the CN, CI, FN, and FI abnormal relationships and the percentages of each of these abnormal of these abnormal relationships is indicated. In each of these sections, the mean degree of abnormality (in BU) of the represented abnormal parameter is also indicated, as is the statistical coefficient of variation (CV) of such abnormal parameters. (No mean or CV is indicated in FIG. 6A or 6B because these sections represent parametric relationships with quantitatively normal values).

It will be appreciated that the charts of FIG. 5 will present significantly more comprehendible information to a trained person than numerical data alone, or prior art charts. Also follow up evaluation is greatly facilitated by comparing charts for a patient at sequential stages of a disease.

In fact, in U.S. Pat. No. 4,527,240 considers four tools suitable for graphical representation and analysis of multiple parameters in their interrelationships. More specifically, the first tool was described with reference to FIG. 1 and may be named "analysis of pairs"; the second tool was described with reference to FIGS. 2 and 3 and may be names "circular diagram method"; the third tool was described with reference to FIG. 4 and may be names "matrix representation method"; and the fourth method was described with references to FIG. 5 and may be named "multiple relationship graphs method".

Each of the aforementioned tools, may be used individually or in combinations. However, these tools still possess a number of disadvantages which does not allow to use to full extent the potentials inherent in statistical data. A main disadvantage of the first tool, which has been described with reference to FIG. 1, is that it does not present a sufficient quantitative information required for evaluation of relationships between the interconnected pairs of parameters.

Even though the graphs of FIG. 1 have scales, it is not convenient to use these scales for quantitative evaluation. Furthermore, this method is time-consuming and is not sufficiently illustrative.

The circular diagrams shown in FIGS. 2 and 3 are not sufficiently convenient for distinguishing between various diseases because of great diversity of shapes of polygons formed by connecting points on the radial axes. Even those polygons which are plotted for one and the same disease may exist in such great variety that it would difficult to reveal an actual disease with sufficient accuracy. Thus, in spite of certain usefulness, the method based on graphical representation in a circular coordinate system cannot be used along and, as a rule, require combination with one or both other methods.

An advantage of the matrix representation method of FIG. 4 is that it may contain a sufficient quantitative information, including the statistic data introduced through the use of balascopic units. However, it is obvious that this method is not sufficiently illustrative graphically as it shows only the numbers.

Finally, the fourth tool, i.e., the multiple relationship graphs method, which demonstrated normal or abnormal specific relationships between many parameters in the form of a planar graph, is purely qualitative and does not contain any quantitative information.

In view of the above disadvantages, the existing balascopic methods are not sufficiently sensitive for accurate diagnosing, and the four tools described in the previous patent of the applicant diseases should be used only in combination of at least two, and preferably of all four. It is understood that for using the advantages of the balascopic approach to full extent, the above methods need to be modified and improved.

OBJECTS AND SUMMARY OF THE INVENTION

It is an object of the present invention to provide a balascopic method and system which combine two or more of the previous system analysis tools in one. Another object is to improve each existing balascopic tool individually. Still another object is to improve sensitivity of the balascopic methods in diagnosing diseases. A further advantage is to improve informativity of the balascopic method simultaneous with simplification of representation methods. Another object is to provide a balasopic method and system for presenting a qualitative, quantitative, and pictorial information in a single graph.

The method and system of the present invention improve and further develop the balascopic concept disclosed in U.S. Pat. No. 4,527,240. The "analysis-of-pair" method is improved and simplified by replacing the graphical linear representation of FIG. 1 by so-called balascopic vectors, which show a direction of changes of the relationship from normal and the length of which corresponds to the amount of the change. The normal relationships are expresses by scalar values in the form of vertical linear sections, while deviations from the normal are expressed by vertical vectors having lengths corresponding to the magnitude of the deviation. The circular diagram method is improved by dimensisonlessly resealing the balascopic unit of FIGS. 2 and 3 into a system in which deviations for all parameters are shown from mean statistic values recalculated on the same radius of the circular diagram. The diagrams show three substantially concentric circles, of which the inner circle corresponds to the minimal normal values, the outer circle corresponds to the maximal normal values, and the intermediate circle corresponds to the mean statistic values. The latter are assumed as 100% normal value of corresponding parameters. With the use of such converted system, it becomes possible to present all deviations of diagnostic parameters from normal condition in more visually obvious form and in a relative balascopic units, hereinafter referred to as "relative balascopic units". According to another embodiment for balascopic representation of diagnostic data, the circular diagrams of the invention are developed into a linear form which is more convenient for observing the dynamics of the disease by arranging the graphs plotted at time intervals, one beneath the other.

The matrix representation method is improved by rearranging the parameters into a conventional orthogonal matrix, wherein the diagonal cells contain balascopic units combined with values of the parameters measured in natural units of these parameters, and wherein other cells contain values and symbols that characterize magnitude of the change in relationships in comparison with normal relationships. The invention also improves the multiple relationship graphs by showing not only links between all normal and abnormal parameters with specific relationships, but also the sign of the change relative to normal change in terms of vectors, while the length of the vector shows the absolute value of the change.

BRIEF DESCRIPTION OF THE DRAWINGS

FIG. 4 is a prior-art diagram that shows parametric qualitative relationships between the diagnostic parameters in a matrix form.

FIGS. 5A through 5F are prior-art graphs which shown pair of parameters with specific relationships indicated by lines interconnecting the pair of dots representing the parameters.

FIG. 10 is an improved matrix representation of the diagnostic parameters in accordance with the invention.

DETAILED DESCRIPTION OF THE INVENTION

Figure 1:
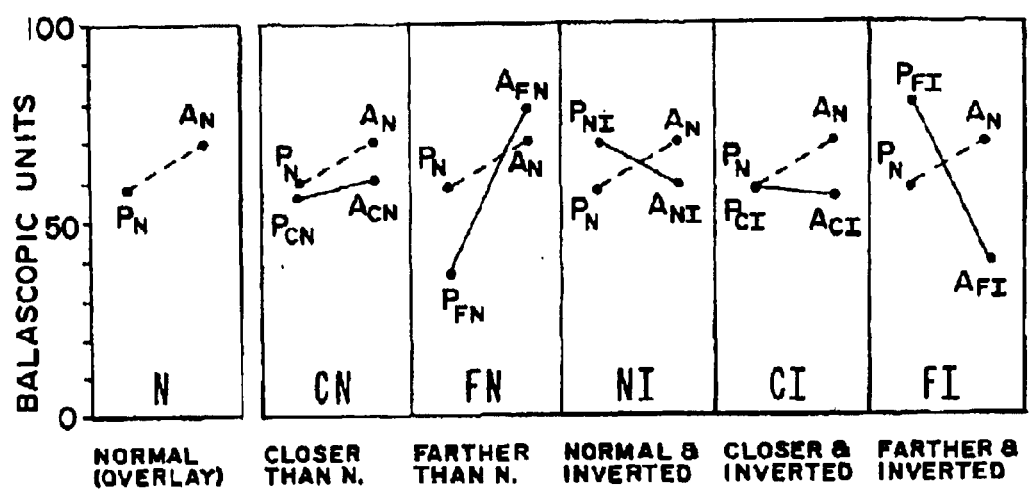
FIG. 1 is a prior-art graph illustrating normal relationship between pairs of diagnostic data and various deviations from the norm.
Figure 6:
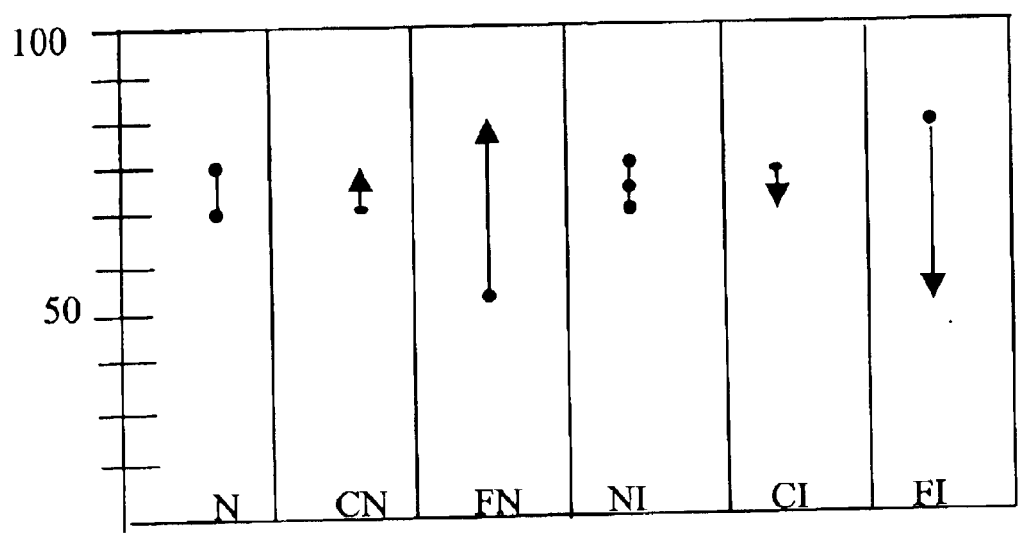
FIG. 6 is a graph of the present invention similar to FIG. 1 but simplified and improved by introducing balascopic vectors that show directions of changes of the relationship from normal and the amount of the change.

The invention will now be described in more detail with reference to the attached drawings, wherein FIG. 6 is a graph of the present invention similar to FIG. 1 of the prior-art method but simplified and improved by introducing balascopic vectors that show directions of changes from the normal relationships and the amount of the change. More specifically, similar to FIG. 1, the graph of FIG. 6 consists of six sections, which illustrate six types of relationships between the diagnostic parameters and the nature and amount of changes in these relationships. The normal relationships shown in the section designated by symbols N and NI are expresses by scalar values in the form vertical lines. NI designates normal inverted relationships. While the normal N and normal-inverted relationships NI are expressed as scalars, all other relationships, which are deviated from normal, are expressed by vectors and are designated as CN (closer than normal), FN (further then normal, etc.), the lengths of the vectors corresponding to the magnitude of the deviation and can be evaluated with reference to the scale S shown on the left side of the graph. In order to simplify graphical distinctions between N and NI, a dot is placed in the middle of the NI line. Thus, in the graph of FIG. 6, the scolar length in section N is 11 BU, the length of the vector in CN is 5 BU, the length of the vector in FN is 40 BU, the length of the scolar in NI is −11 BU, the length of the vector in CI is −5 BU and the length of the vector in FI is −40 BU.

If necessary, however, the scolar length of the normal relationships (N) can be assumed as 100% and the length of the other scolar and of all the vectors can be expressed in relative balascopic units, i.e., as percents of deviation from the normal scolar length shown in section N and taken as 100%. In this case, the following values will be obtained for the respective sections of the graph of FIG. 6: N=100%, CN=45.5%, FN=363.6%; NI=−100%; CI=−45.5% FI=−363.6%. These numbers are shown above the scolars and vectors.

Figure 2:
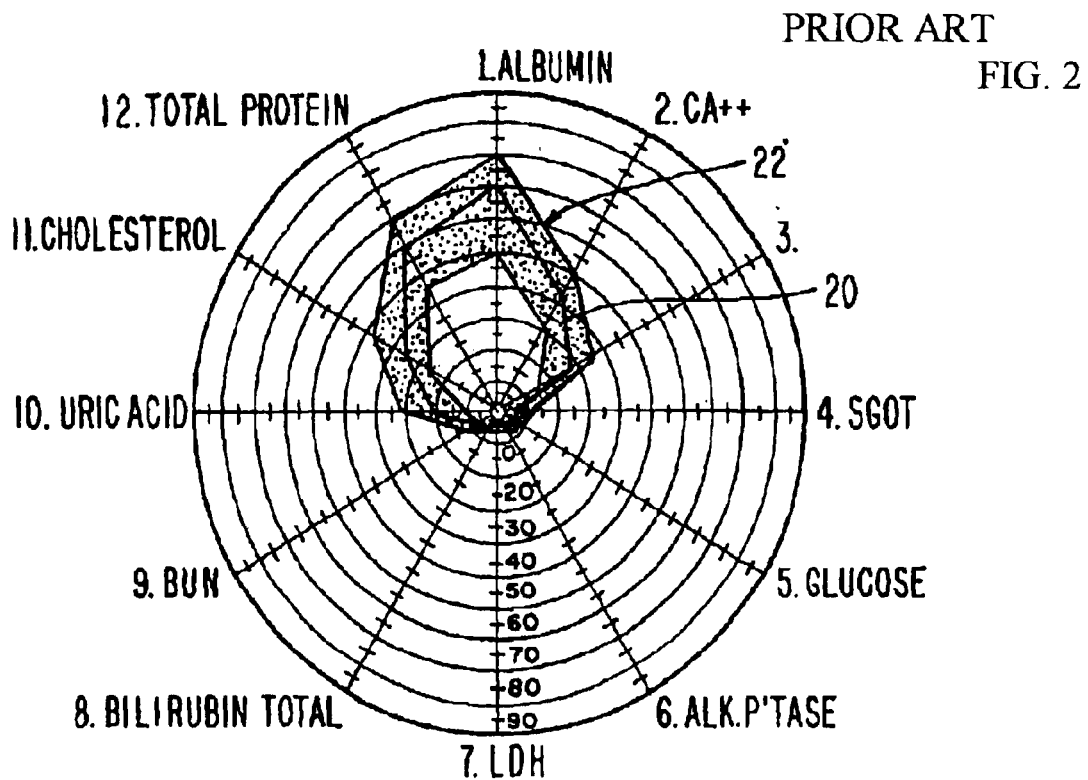
FIG. 2 is a prior-art circular diagram of a balascopic pattern for blood chemistry that contains shaded closed-loop area, which limits the boundaries for normal patterns.
Figure 3:
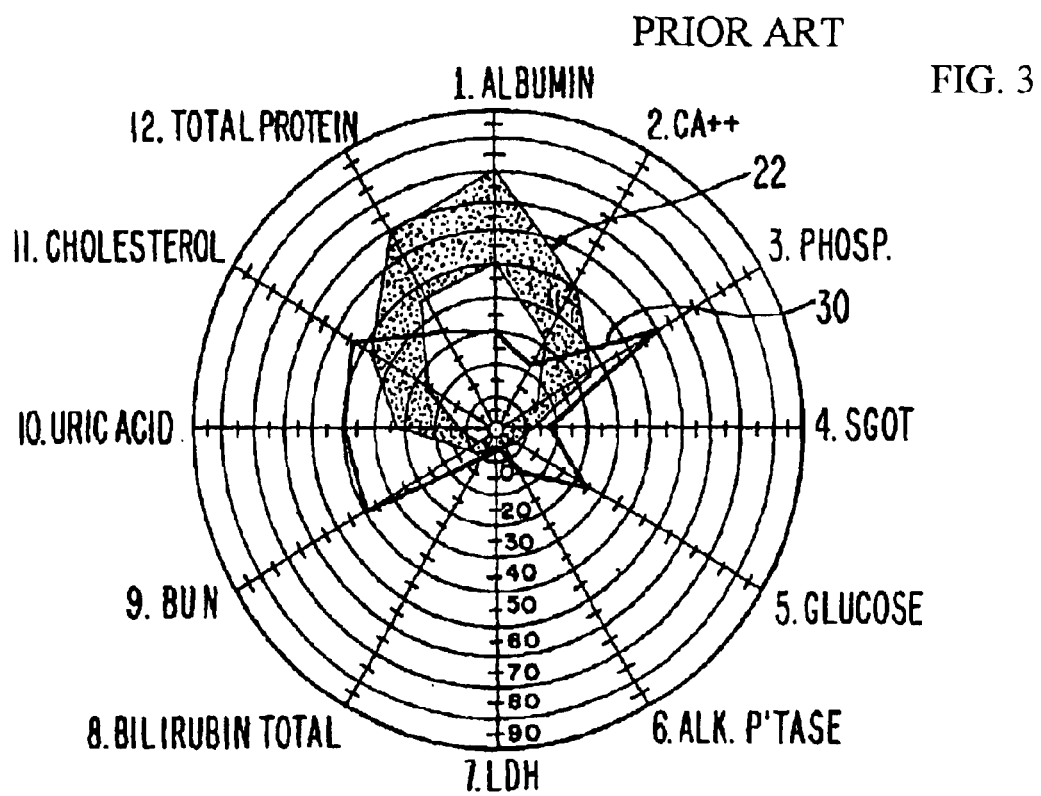
FIG. 3 is a prior-art circular diagram similar to FIG. 2 but depicting abnormal patterns of blood chemistry typical for a patient with *diabetes mellitus* with Kimmelstiel-Wilson disease and secondary hyperparathyroidism plotted on the background of the normal area.
Figure 7:
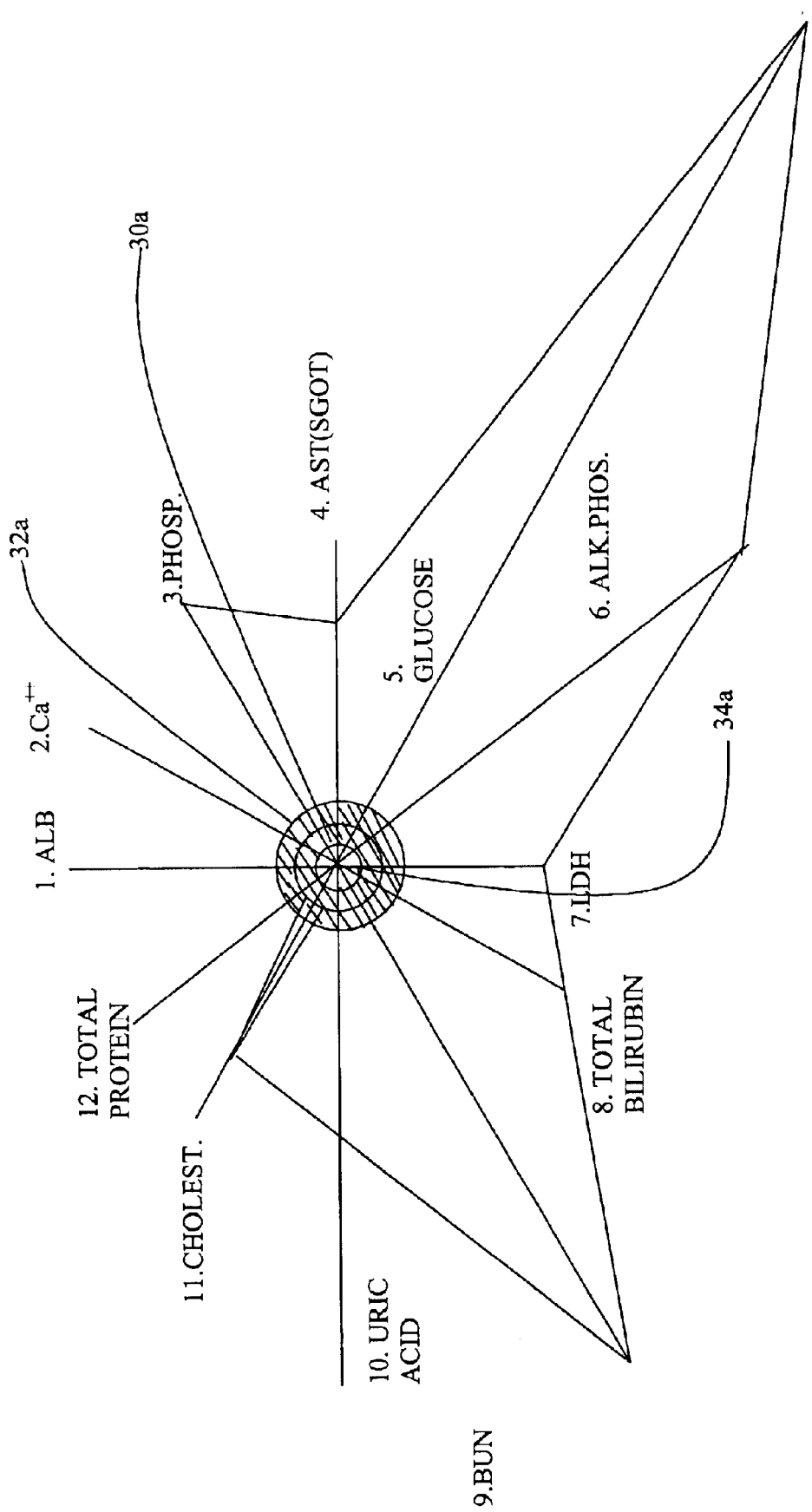
FIGS. 7 and 8 are circular diagrams of the invention which dimensionlessly rescale the balascopic units of FIGS. 2 and 3 into a system in which deviations for all parameters are shown from mean statistic values recalculated on the same radius of the circular diagram.
Figure 8:
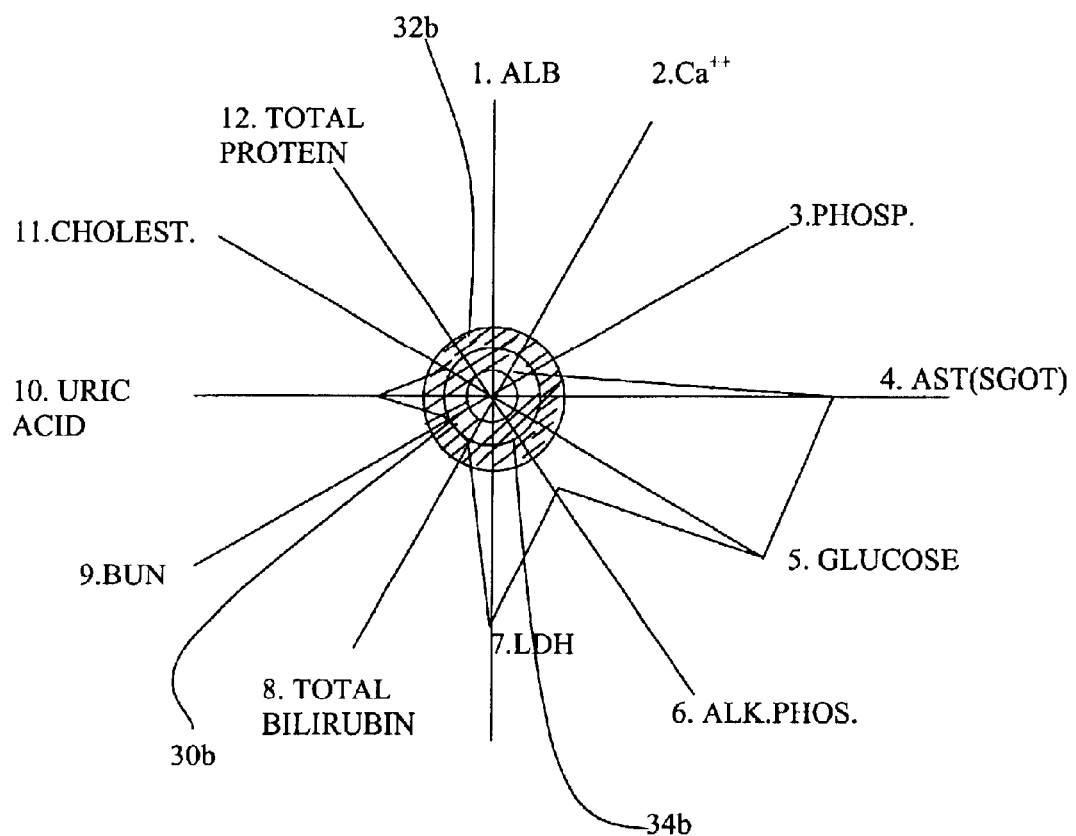

According to the present invention, the circular diagram method of U.S. Pat. No. 4,527,240 is improved by dimensionlessly resealing the balascopic units of FIGS. 2 and 3 into a system in which deviations for all parameters are shown from mean statistic values recalculated on the same radius of the circular diagram. Mathematically, such a conversion is known as the affine conversion, which in this case is made in the circular coordinate system shown in FIGS. 7 and 8. The diagram of FIG. 7 is plotted on the basis of the same data that has been used for plotting the diagram of FIG. 3 (i.e. for diagnosing *Diabetes mellitius* with Kimmel Stiel-Wilson disease and Z° Hyperparathyroidism), while the diagram of FIG. 8 is plotted on the basis of data corresponding to myocardial infarct.

In these drawings, the diagrams show three substantially concentric circles, of which the inner circles 30*a*, 30*b* correspond to the minimal normal values, the outer circles 32*a*, 32*b* correspond to the maximal normal values, and the intermediate circles 34a, 34b correspond to the mean statistic values. The mean statistic value on each radial axis (1.ALB, 2.$Ca^{++}$, 3. PHOSP, etc.) of FIGS. 7 and 8 is assumed as 100% normal value of a corresponding parameter. In other words, the intermediate circles 34a, 34b are geometrically ideal circles. With the use of such a converted system, it becomes possible to present all deviations of diagnostic parameters from normal condition in a more visually obvious form and in a relative balascopic units.

Figure 9:
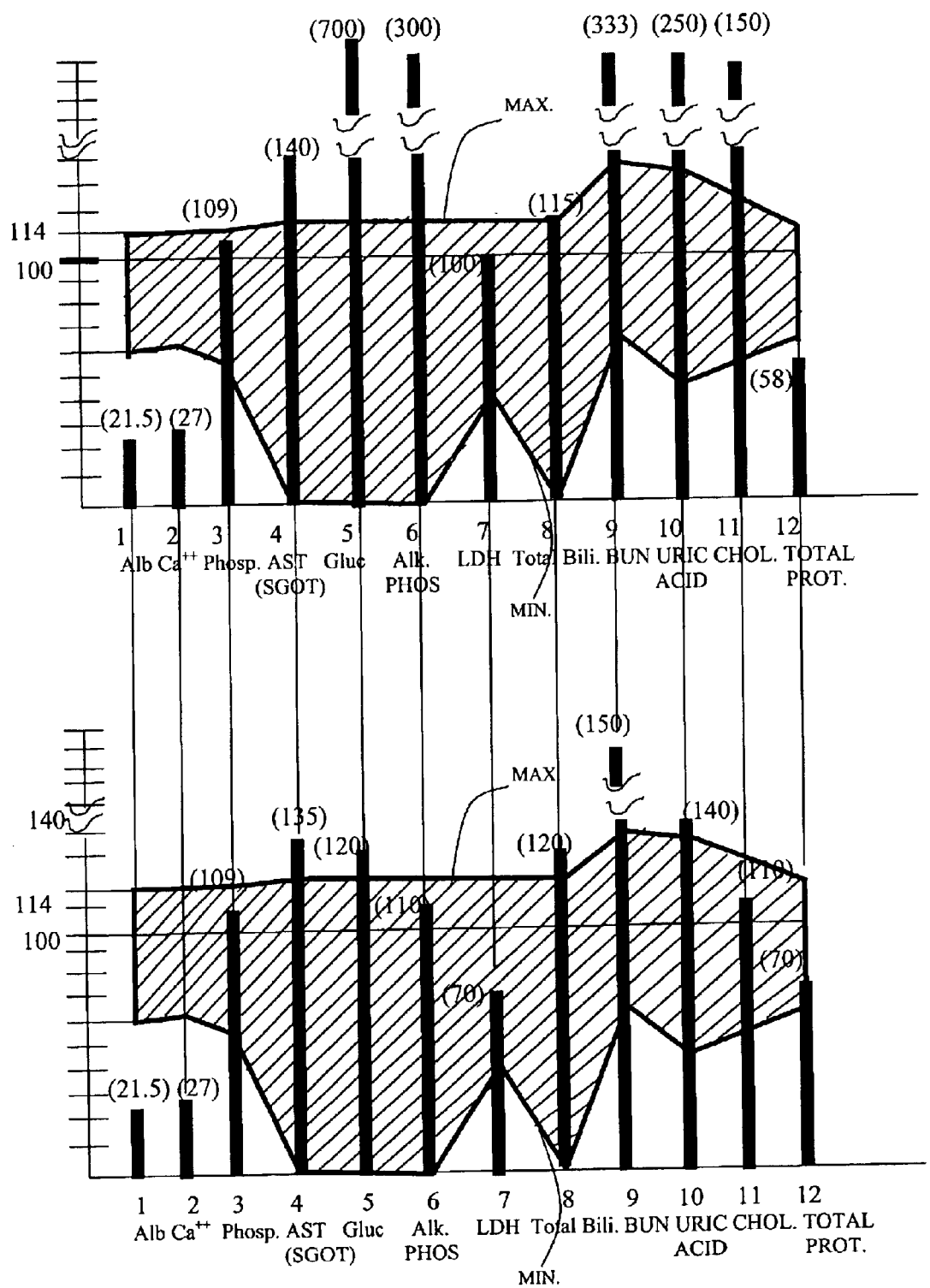
FIG. 9 illustrates another embodiment of the invention, in which the circular diagrams of FIGS. 7 and 8 are developed into a linear form for observing dynamics of variations in the relationships by arranging the sequential graphs one underneath the other.

FIG. 9 shows another embodiment for balascopic representation of diagnostic data. In fact, this diagram is a linear development of the circular diagrams shown in FIGS. 6 and 7. The abscissa axis is used for vertical axes of the parameters which are arranged in a predetermined sequence. The ordinate axes are used for plotting values of the parameters in terms of relative balascopic units with respect to the norm. The norm is shown by the horizontal line with the ordinate of 100%. The upper curve MAX is the boundary of the maximal normal value, and the lower curve MIN is the boundary of the minimal normal value. Such a representation is more convenient for observing the dynamics of the disease by arranging the graphs plotted at time intervals, one beneath the other. From comparison of the upper and lower graphs of FIG. 9, one can see that the lower graph plotted after a certain time period shows improvement in the condition of some parameters as a result of treatment.

FIG. 10 is an improved matrix representation of the diagnostic parameters in accordance with the invention. As can be seen from FIG. 10, the matrix representation method is improved by rearranging the parameters into a conventional orthogonal matrix. In this matrix, the horizontal rows and vertical columns correspond to the same numbers that designate various diagnostic parameters on the graphs of FIGS. 2, 3, 5, 7, etc. In other words, 1 designates albumin, 2 designates $Ca^{++}$, 3 designates phosphor, etc. The diagonal cells that are located on intersections of equally-numbered columns and lines of the matrix of FIG. 10, contain relative balascopic units (upper numbers) combined with values of the parameters measured in natural units of these parameters (lower numbers). Other cells contain values and symbols that characterize magnitude of the change in relationships in comparison to normal relationships (i.e., FN—further than normal, CN—closer than normal, etc.).

The matrix for blood-analysis parameters shown in FIG. 10 has 12 horizontal rows and 12 vertical columns and therefore contains 144 matrix cells. Of these cells, 132 cells may describe specific relationships between any two specific parameters. It can be seen that the part which is on the left side of the diagonal of the matrix contains inverted relationships, while the right side contains cells of normal and transformed normal relationships. Since relationships between the parameters designated by reversed numbers, e.g., 2–7 and 7–2, etc., are identical, the part of the matrix on the left of the diagonal is used only for convenience and for grouping of all inverted relationships. Thus, the actual number of unequivocal relationships will be equal to 132:2= 66. As has been mentioned above, I selected 6 types of relationships, such N, CN, FN, IN, CI, FI. In other words, in my example, I selected 6 possible gradations of relationships for blood-analysis parameter. It is understood that in general there could be other relationships and in larger or smaller amount. Thus, the total amount of theoretically possible different matrix states in the 12-parameter balascopic system will be 66×6=396. This means that any analysis of parameter relationships will fall into one of different 396 states.

The matrix representation of the type shown in FIG. 10, makes it possible to further consider relationships between individual cells of the matrix, which we may call "second-order relationships". It is understood that such second-order relationships also may characterize different states of a patient and therefore may be used for more sophisticated analysis. Thus, in the illustrated example, where the number of possible different states is 396, the number of combinations between the different states will be equal to 25740. It is understood that only those of these total states which are useful will be used.

In other words, the aforementioned relationships of the second order are relationships not between the parameters but rather between different parametric data of these parameters.

In fact, the matrix-type representation contains a very detailed information which, however, is not sufficiently obvious for an unskilled person. After acquiring some habits in the usage of the last-mentioned method, it would be possible to quickly interpret all the deviations from the normal relationships in connection with the disease associated with such changes.

Figure 11A:
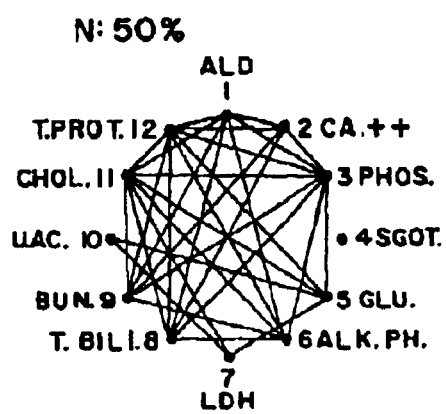
FIGS. 11A–11C are graphs of the invention that show links between all normal and abnormal parameters with specific relationships, signs of changes relative to normal change, and absolute values of the changes.
Figure 11B:
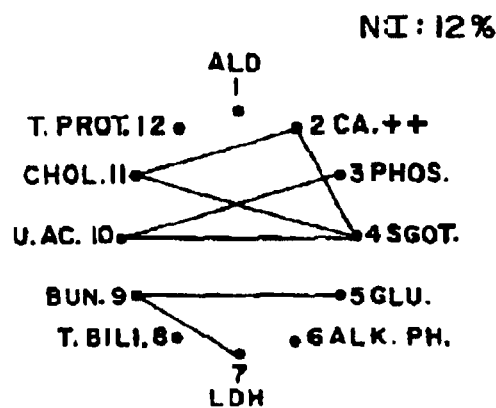
Figure 11C:
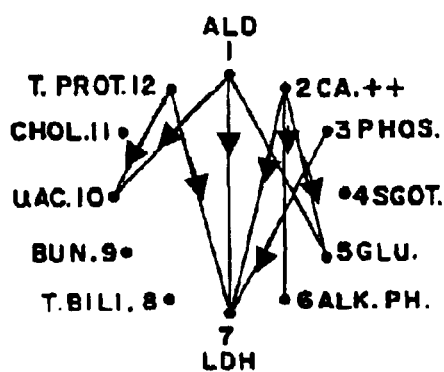

The information contained in the matrix of FIG. 10 may be presented in a more obvious and explicit form and may combine in itself all three previous methods. This is illustrated by the graphs shown in FIGS. 11A–11C, which show multiple links between all normal and abnormal parameters with specific relationships. The sign of changes relative to normal corresponds to the direction of vectors that connect the pairs of parameters, while the lengths of the vectors show the absolute values of changes in the relationships. FIG. 11A corresponds to normal specific relationships. Therefore the links comprise scolars, which can be interpreted as links between two parameters which are in a specific equilibrium (healthy individuals). FIG. 11B shows only abnormal NI relationships. The higher is the number of lines in this graph, the worse are the patient's conditions. In this case the links are presented by vectors, where the lengths of the vectors correspond to the degree of deviation from the normal relationship, while the direction of the vector shows direction of the change. Since plotting of such graphs may cause problems when the range of changes from small to large are significant, the graphs of FIGS. 11A–11C are shown not on scale. FIG. 11C also shows abnormal relationship but for the CN case. Graphs for other types of changes in relationship (FN, CI, etc.) are not shown.

Figure 12A:
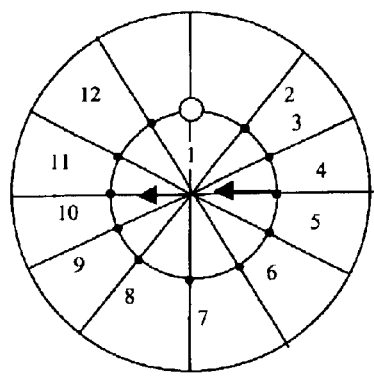
FIGS. 12A–12D are graphs in accordance with another embodiment of the invention for showing links between all normal and abnormal parameters with specific relationships, signs of changes relative to normal change, and absolute values of the changes.
Figure 12B:
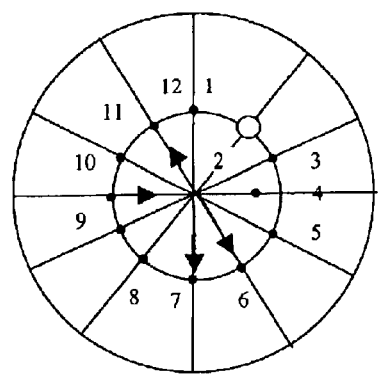
Figure 12C:
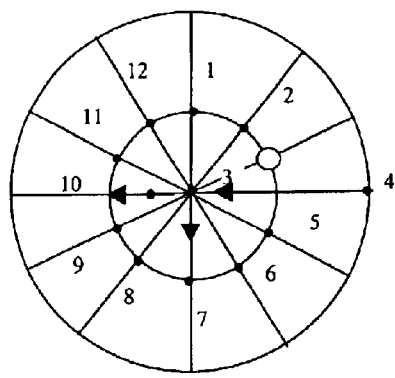
Figure 12D:
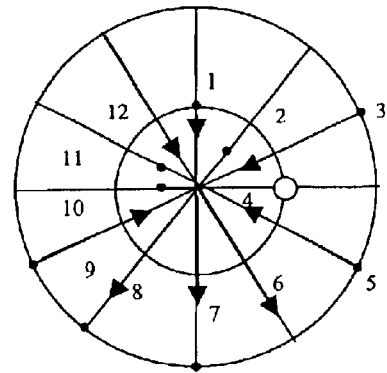

Since the graphs of FIGS. 11A–11C may be difficult to plot, they can be replaced by the graphs of the type shown in FIGS. 12A–12D. More specifically, one of the points that designates one of the chosen parameters is place into a point of origin of a circular diagram. Values of other parameters in relative balascopic units are plotted on radii extending from the aforementioned point of origin. As some of the values may be significantly greater (e.g., more than 100 times greater) than values of other parameters, it is recommended to plot the parameters in the radii on a logarithmic scale. For example, the first concentric circle C1 will correspond to 100%, the second circle spaced on a distance of a double radius will correspond to 1000%, the next one to 10000%, etc. FIG. 12A shows relationships between parameter 1 (Albumen) and the remaining 11 parameters. The lengths of the vectors correspond to the magnitude of the relationship change in the balascopic system. FIG. 12B shows relationships between parameter 2 ($Ca^{++}$) and the remaining 11 parameters, while FIG. 12C shows relationships between parameter 3 (Ph) and the remaining 11 parameters. FIG. 12D shows relationships between parameter 4 AST(SGOT) and the remaining 11 parameters. Other relationships are not shown.

Thus it has been shown that the invention provides a balascopic method and diagrams which simplifies interpretation of balascopic data and relationships between parameters of a multiparametric system, improve sensitivity of the balascopic analysis, and presents analysis data in the most obvious and easily understandable form. The invention also provides the diagnosing method and diagrams which make it possible to combine a qualitative, quantitative, and pictorial information in a single graph.

The invention has been shown and described with reference to specific embodiments which should be construed only as examples and do not limit the scope of practical applications of the invention. Therefore any changes and modifications in materials, shapes, electric diagrams and their components are possible, provided these changes and modifications do not depart from the scope of the patent claims. For example, it is understood that for different social, age, race, occupational, climatic and other groups of population the aforementioned normal mean statistical data may be different, even at all other conditions being equal. For example, mean statistical data of blood analysis for teenagers will have values different from the same blood analysis data for elderly people. The same deviations can be observed for population groups having distinctly different diet, e.g., those who live in the far north and in equatorial countries. It is also understood that the diagrams and method of the invention are applicable to multiparametric systems other than blood. For example, the approach of balascopic statistical analysis can be used for such muiltiparametric systems as the result of urinalysis, analysis of saliva, marrow, stomach juice, etc. Similar systems may be analyzed in combinations with each other. For example, for some diseases, which are characterized by changes observed in both blood analysis and urinalysis, the data can be combined into a single system with an increased number of points on the graphs, diagrams, and in the matrices. It is understood that the method and diagrams of the invention are not limited to the representations described in the specification and that data can be presented in many other forms, e.g., in the form of three-dimensional graphs, provided that the principle of percent (relative) balascopic units is used. If the relative balascopic units of different parameters vary in very wide ranges, it would be convenient to present the data on a logarithmic scale.

I claim:

1. A method of evaluating data for a plurality of parameters in a multi-parametric system, comprising the steps of:
    (a) obtaining a plurality of parametric data for said parameters of said multi-parametric system;
    (b) converting each of said parametric data into balascopic units;
    (c) providing a known reference data for each of said parametric data in said balascopic units;
    (c) converting said balascopic units of each of said parametric data into relative balascopic units relative to said known reference data which is taken as 100%;
    (d) further converting said relative balascopic units into a graphical form selected from a group consisting of a linear vector/scolar form, a matrix form, a circular diagram form, a linear diagram form obtained by developing said circular diagram form, and a multiple link form which shows connections between at least a part of said parameters having specific relationships; and
    (e) evaluating said multi-parametric system by comparing said graphic forms with a known reference graphic form plotted on the basis of said known reference data of said multi-parametric system.

2. The method of claim 1, wherein said known reference data comprises a mean normal statistic value of said parametric data and wherein for each of said parametric data said relative balascopic units are obtained by multiplying each said parametric data by 100 and dividing the obtained product by the number of balascopic units contained in said mean normal statistic value of said parametric data.

3. The method of claim 2, wherein said step of converting into said linear vector/scolar form comprises:
    a. finding specific relationships between pairs of said parameters;
    b. classifying said specific relationships into relationships types;
    c. providing a common axis for plotting said relative balascopic units on said common axis; and
    plotting said parametric data for each of said relationship types plotted in said relative balascopic units on axes parallel to said common axes and in alignment therewith.

4. The method of claim 3, wherein said specific relationships comprises a group that contains at least normal relationships (N), closer-than-normal relationships (CN), further-than-normal relationships (FN), normal-inverted relationships (NI), closer-inverted relationships (CI), and further-inverted relationships (FI).

5. The method of claim 4, wherein said normal relationships (N) and said normal-inverted relationships (NI) are described by scolar linear sections and wherein said closer-than-normal relationships (CN), further-than-normal rlationships (FN), closer-inverted relationships (CI), and further-inverted relationships (FI) are described by vectorial linear sections, said scolar linear sections and said vectorial linear sections being arranged parallel to said common axis.

6. The method of claim 5, further comprising a step of determining direction of change in said closer-than-normal relationships (CN), further-than-normal relationships (FN), closer-inverted relationships (CI), and further-inverted relationships (FI) from said normal relationships.

7. The method of claim 2, wherein said steps of converting into said linear diagram form comprises:
    (a) providing linear axes, one for each of said parameters, calibrated in said relative balascopic units;
    (b) arranging said linear axes of said parameters parallel to each other;
    (c) calibrating said linear axes in said relative balascopic units;
    (d) determining minimal normal statistic values and maximal normal statistic values for each of said parameters;
    (e) determining normal mean statistic value of said parameters;
    (f) converting said minimal normal statistic values, maximal normal statistic data, and said normal mean statistic values into said relative balascopic units;
    (g) plotting said relative balascopic units of said minimal normal statistic values, maximal normal statistic data, and said normal mean statistic values on said radial axes;
    (f) creating a minimal normal linear pattern, a maximal normal linear pattern, and mean normal linear pattern by interconnecting points of maximal, minimal, and normal mean values on adjacent ones of said parametric axes;
    (g) plotting said relative balascopic units of said parametric data on said linear axes for obtaining a parametric linear pattern; and (g) evaluating said multi-parametric system by comparing the position of said parametric linear pattern with respect to positions of said a minimal normal linear pattern and maximal normal linear pattern.

8. The method of claim 7, further comprising the steps of:
providing at least one more linear diagram form after a predetermined period of time by repeating said steps from (a) to (g) of claim 7, and plotting said at least one more linear diagram on the same linear axes as in claim 7, arranging said at least one more linear diagram under said linear diagram of claim 7, and aligning respective linear axes of said linear diagram of claim 7 with respective axes of said at least one more linear diagram; and
analyzing the dynamics of change that occurred in said multiparametric system during said certain period of time by observing variations that occurred in said relative balascopic units on aligned axes of said linear diagram of claim 7 and of said at least one more linear diagram.

9. The method of claim 8, wherein said specific relationships comprise a group that contains at least normal relationships (N), closer-than-normal relationships (CN), further-than-normal relationships (FN), normal-inverted relationships (NI), closer-inverted relationships (CI), and further-inverted relationships (FI).

10. The method of claim 9, further comprising the steps of:
establishing second-order relationships between at least two different cells of said matrix; and
analyzing said multiparametric system on the basis of said second-order relationships.

11. The method of claim 2, wherein said step of converting into said matrix form comprises:
forming an orthogonal matrix with the same parameters arranged on equally numbered horizontal rows and vertical columns so that diagonal cells are located on intersections of said equally-numbered rows and columns;
determining specific relationships between pairs of said parameters and arranging said specific relationships in the matrix cells formed by intersections of parameters of said pairs; and
placing in said diagonal cells parametric data of said parameters at least in terms of said relative balascopic units.

12. The method of claim 11, wherein said specific relationships comprise a group that contains at least normal relationships (N), closer-than-normal relationships (CN), further-than-normal relationships (FN), normal-inverted relationships (NI), closer-inverted relationships (CI), and further-inverted relationships (FI).

13. The method of claim 12, further comprising the steps of:
establishing second-order relationships between at least two different cells of said matrix; and
analyzing said multiparametric system on the basis of said second-order relationships.

14. The method of claim 11, additionally placing in said diagonal cells natural values of said parametric data of said parameters.

15. The method of claim 2, wherein said conversion into said multiple link form which shows connections between at least a part of said parameters having specific relationships comprises the steps of:
designating said parameters of said multi-parametric system with specific designations;
establishing a circular coordinate system with a center of origin and a plurality of radii extending from said center of origin with the number of radii equal to the number of said parameters;
designating said radii with said specific designations which correspond to said parameters;
selecting one of said parameters and placing said specific designations of one of said parameters into said center of origin;
plotting values of changes in said specific relationships between said one of said parameters and other of said parameters on said respective radii in said relative balascopic units starting from said point of origin; designating a direction of said changes by vectors; and
showing the amount of said changes by the lengths of said vectors.

16. The method of claim 15, further comprising the step of indicating the absolute values of said changes in relationships by attaching a number to each said vector.

17. The method of claim 16, further comprising a step of plotting said said values of changes on said radii on a logarithmic scale.

18. The method of claim 15, further comprising a step of plotting said values of changes on said radii on a logarithmic scale.

19. The method of claim 2, wherein said conversion into said multiple link form which shows connections between at least a part of said parameters having metabolic relationships comprises the steps of:
designating all parameters of said multi-parametric system by dots with specific designation of each of said parameters;
connecting the dots of at least a part of said parameters which have specific relationships by multiple links;
determining links between parameters having normal relationships and abnormal relationships;
designating said links of said abnormal relationships by vectors with directions of said vectors showing the direction of change of said relationships relative to said normal relationship; and
showing the amount of said changes by the lengths of said vectors.

20. The method of claim 19, further comprising the step of indicating absolute values of said changes in relationships by attaching a number to each said vector.

21. The method of claim 2, wherein said steps of converting into said circular diagram form comprises:
(a) providing a circular coordinate system having radial axes corresponding to said parameters of said multi-parametric system, each axis being calibrated in said relative balascopic units;
(b) determining minimal normal statistic values and maximal normal statistic values of said parameters;
(c) determining normal mean statistic values of said parameters;
(d) converting said minimal normal statistic values, maximal normal statistic data, and said normal mean statistic values into said relative balascopic units;
(e) plotting said relative balascopic units of said minimal normal statistic values, maximal normal statistic data, and normal mean statistic values on said radial axes;
(f) creating a minimal dosed-loop pattern, a maximal closed-loop pattern, and normal mean closed-loop area by interconnecting points of maximal, minimal, and normal mean values on adjacent ones of said radial axes;

(g) plotting said relative balascopic units of said parametric data on said axes; and (g) evaluating said multi-parametric system by comparing said closed configuration patterns with the area between said minimal closed-loop pattern and said maximal closed-loop pattern.

22. The method of claim 1, wherein the number of said parameters is n, the number of the types of said specific relationships is m, and the maximum possible number of links between pairs of said parameters is a number of combination of n by 2.

23. The method of claim 22, wherein said known reference data comprises a mean normal statistic value of said parametric data and wherein for each of said parametric data said relative balascopic units are obtained by multiplying each said parametric data by 100 and dividing the obtained product by the number of balascopic units contained in said mean normal statistic value of said parametric data.

24. The method of claim 23, wherein said step of converting into said linear vector/scolar form comprises:

a. finding specific relationships between pairs of said parameters;

b. classifying said specific relationships into said types of said specific relationships;

c. providing a common axis for plotting said relative balascopic units on said common axis; and plotting said parametric data for each of said types of specific relationships plotted in said relative balascopic units on axes parallel to said common axes and in alignment therewith.

25. The method of claim 22, wherein said step of convening into said matrix form comprises:

forming an orthogonal matrix with said n parameters arranged on equally numbered horizontal rows and vertical columns so that diagonal cells are located on intersections of said equally-numbered rows and columns;

determining said types of specific relationships between pairs of said n parameters and arranging said types of specific relationships in the matrix cells formed by intersections of parameters of said pairs; and placing in said diagonal cells parametric data of said parameters at least in terms of said relative balascopic units.

26. A system for evaluating data for a plurality of parameters in a multi-parametric system, comprising:

(a) a plurality of parametric data for said parameters of said multi-parametric system, said parametric data being converted into relative balascopic units, wherein said relative balascopic units being obtained by multiplying each said parametric data by 100 and dividing the obtained product by the number of conventional balascopic units contained in a mean normal statistic value of said parametric data;

(b) a graphic representation of said parametric data in said relative balascopic units selected from a group consisting of a linear vector/scolar representation, a matrix representation, a circular diagram representation, a linear diagram representation obtained by developing said circular diagram representation, and a multiple link representation, which shows connections between at least a part of said parameters having specific relationships; and (c) a graphic representation of a known reference data of said parameters in the same representation forms as those selected for said parametric data in item (b) for comparison with said parametric data of said multi-parametric system.

27. The system of claim 26, wherein said known reference data comprises a mean normal statistic value of said parametric data.

28. The system of claim 27, wherein said linear vector/scolar representation comprises:

at least two pairs of said parameters having specific relationships which are classified by relationship types with specific designation of said relationship types;

a common axis for plotting said relative balascopic units on said common axis; and parametric data for each of said relationship types plotted in said relative balascopic units on axes parallel to said common axes and in alignment therewith.

29. The system of claim 28, wherein said specific relationships comprises a group that contains at least normal relationships (N), closer-than-normal relationships (CN), further-than-normal relationships (FN), normal-inverted relationships (NI), closer-inverted relationships (CI), and further-inverted relationships (FI).

30. The system of claim 29, wherein said normal relationships (N) and said normal-inverted relationships (NI) are described by scolar linear sections and wherein said closer-than-normal relationships (CN), further-than-normal relationships (FN), closer-inverted relationships (CI), and further-inverted relationships (FI) are described by vectorial linear sections, said scolar linear sections and said vectorial linear sections being arranged parallel to said common axis.

31. The system of claim 30, wherein said linear diagram representation comprises:

(a) a plurality of linear axes, one for each of said parameters, calibrated in said relative balascopic units and arranged in alignment with and parallel to each other;

(b) minimal normal statistic value, maximal normal statistic values for each of said parameters; and normal mean statistic value of said parameters plotted in said relative balascopic units on said linear axes;

(c) a minimal normal linear pattern, a maximal normal linear pattern, and a mean normal linear pattern formed by interconnecting points of said maximal, minimal, and normal mean values on adjacent ones of said parametric axes;

(d) relative balascopic units of said parametric data plotted on said linear axes for obtaining a parametric linear pattern; and (e) a linear pattern of said parametric data obtained by connecting points of said parametric data on adjacent ones of said linear axes.

32. The system of claim 31, comprising at least one more linear representation of claim 29 plotted on the bases of sad said parametric data obtained after expiration of a predetermined period of time and arranged in a position where said linear axes of said one more linear representation are aligned with the positions of respective axes of said linear representation of claim 29 for possibility of observation of dynamical changes in said parametric data.

33. The system of claim 30, wherein directions of change in said closer-man-normal relationships (CN), further-than-normal relationships (FN), closer-inverted relationships (CI), and further-inverted relationships (FI) from said normal relationships correspond to directions of said vectorial linear sections.

34. The system of claim 26, wherein said matrix representation comprises:

an orthogonal matrix with the same parameters arranged on equally numbered horizontal rows and vertical columns so that diagonal cells are located on intersections of said equally-numbered rows and columns;

specific relationships between pairs of said parameters indicated in the matrix cells formed by intersections of parameters of said pairs; and at least said parametric data being indicated in said diagonal cells of said matrix at least in terms of said relative balascopic units.

35. The system of claim 34, additionally indicating in said diagonal cells natural values of said parametric data of said parameters.

36. The system of claim 35, wherein said specific relationships comprises a group that contains at least normal relationships (N), closer-than-normal relationships (CN), further-than-normal relationships (FN), normal-inverted relationships (NI), closer-inverted relationships (CI), and further-inverted relationships (FI).

37. The system of claim 34, wherein said specific relationships comprises a group that contains at least normal relationships (N), closer-than-normal relationships (CN), further-than-normal relationships (FN), normal-inverted relationships (NI), closer-inverted relationships (CI), and further-inverted relationships (FI).

38. The system of claim 26, wherein said multiple-link representation comprises:

a circular coordinate system with a center of origin and a plurality of radii extending from said center of origin with the number of said radii equal to the number of said parameters, wherein each of said radii corresponds to a one of said parameters and wherein the number of said radii is equal the number of said parameters minus 1; one of said parameters being designated by a dot coinciding with said center of origin, while the remaining of said parameters being designated by dots plotted on said radii corresponding to said respective parameters in said relative balascopic units, distances from said center of origin to said dots on said radii being shown by vectors wherein directions of said vectors indicate directions of said change and wherein the lengths of said vectors indicate the amount of said change.

39. The system of claim 38, further comprising numbers indicating absolute values of said change.

40. The system of claim 39, further comprising logarithmic scales on said radii for plotting said dots in relative balascopic units on said logarithmic scales.

41. The system of claim 26, wherein said multiple-link representation between at least a part of said parameters having specific relationships comprises:

designation of said parameters of said multi-parametric system by dots with specific designation of each of said parameters;

connection lines connecting the dots of at least a part of said parameters which have specific relationships;

designation of connection lines between parameters having normal relationships and abnormal relationships;

designation of said connection lines between parameters having said abnormal relationships by vectors with directions of said vectors showing the direction of change of said specific relationships, the lengths of said vectors corresponding to the amount of said change.

42. The system of claim 41, further comprising numbers attached to said vectors and indicating the absolute values of said change in said specific relationships.

43. The system of claim 26, wherein the number of said parameters is n, the number of the types of said specific relationships is m, and the maximum possible number of links between pairs of said parameters is a number of combination of n by 2.

44. The system of claim 43, wherein said known reference data comprises a mean normal statistic value of said parametric data and wherein for each of said parametric data said relative balascopic units are obtained by multiplying each said parametric data by 100 and dividing the obtained product by the number of balascopic units contained in said mean normal statistic value of said parametric data.

45. The system of claim 26, wherein said circular presentation comprises:

(a) a circular coordinate system having radial axes corresponding to said parameters of said multi-parametric system, each axis being calibrated in said relative balascopic units;

(b) minimal normal statistic values, maximal normal statistic values, and normal mean statistic value of said parameters plotted on said radial axes in said relative balascopic units;

(c) a minimal closed-loop pattern, a maximal closed-loop pattern, and normal mean closed-loop pattern formed by interconnecting points of maximal, minimal, and normal mean values on adjacent ones of said radial axes;

(d) relative balascopic units of said parametric data plotted on said radial axes; and (e) a closed-loop configuration pattern of said parametric data formed by interconnecting points of said parametric data on adjacent ones of said radial axes.

* * * * *